United States Patent [19]

Kurono et al.

[11] Patent Number: 4,740,517
[45] Date of Patent: Apr. 26, 1988

[54] ANTIDIABETIC SPIRO-3-HETEROAZOLIDINES

[75] Inventors: Masayasu Kurono, Nagoya; Takuji Yamaguchi, Kuwana; Toshinao Usui, Gifu; Masato Fukushima, Komaki; Kuniharu Mizuno, Aichi; Akira Matsubara, Owari-asahi, all of Japan

[73] Assignee: Sanwa Kagaku Kenyusho Co., Ltd., Aichi, Japan

[21] Appl. No.: 835,823

[22] Filed: Mar. 3, 1986

[30] Foreign Application Priority Data

Mar. 4, 1985 [JP] Japan .................................. 60-41234

[51] Int. Cl.$^4$ ................. A61K 31/415; C07D 491/107
[52] U.S. Cl. ..................................... 514/389; 514/228; 514/231; 514/234; 514/253; 514/278; 514/369; 514/382; 544/70; 544/230; 546/15; 548/147; 548/253; 548/309
[58] Field of Search ....................... 548/309, 147, 253; 544/70, 230; 546/15; 514/278, 231, 228, 234, 253, 389, 369, 382

[56] References Cited

U.S. PATENT DOCUMENTS 4,540,704  9/1985  Ueda et al. ....................... 548/309 X

FOREIGN PATENT DOCUMENTS 1940709  11/1970  Fed. Rep. of Germany ...... 548/308
1220811   5/1960  France ................................. 548/308
 807678   1/1959  United Kingdom ................ 548/308

OTHER PUBLICATIONS

Kinoshita, J., et al., *Jap. J. Opthalmol.*, vol. 20, pp. 399–410 (1976).
Gabbay, K., *Int. Congr. Ser. Excerpta. Med.*, vol. 403, pp. 594–598 (1977).
Peterson, M., et al., *Metabolism*, vol. 28, pp. 456–461 (1979).
*CA*, vol. 69, 2798q (1968) [Canalini, G., et al., *Ann. Chim.* 1967, 57(10), 1045–72].
*CA*, vol. 70, 47334x (1969) [Fravolini, A., et al., *Ann. Chim.* 1968, 58(10), 1155–62].
Kabbe, M. *Synthesis*, pp. 886–887 (1978).

*Primary Examiner*—Richard A. Schwartz
*Attorney, Agent, or Firm*—Armstrong, Nikaido, Marmelstein & Kubovcik

[57]  ABSTRACT

A spiro-3-heteroazolidine compound and agents comprising that compound which have special utility as an antidiabetic composition and as a substance to inhibit aldose reductase enzyme activity.

20 Claims, No Drawings

ANTIDIABETIC SPIRO-3-HETEROAZOLIDINES

BACKGROUND OF THE INVENTION

1. Field of the Invention

The present invention relates to novel spiro-3-heteroazolidine compounds and salts thereof, a process for the preparation of the compounds as well as a pharmaceutical agent comprising at least one of the compounds to cure or prevent a complication due to diabetes.

2. Related Arts

Hithereto, various studies have been made for an effective agent for curing diabetes, which can be orally dosed. As a result, various agents therefor, each of which comprises as an effective component, sulfonyl urea, mesooxalate or guanidine derivative or the like, have been developed and marketed, but those are of a mere symptomatic treating agent to a hypergloycoplasmia due to the diabetes. It has been known there may be caused due to the diabetes specific chronic complications such as diabetic cataract, diabetic neuropathy, diabetic retinopathy and the like but there is almost no effective agent for curing the complications and thus it may be said that no effective therapeutic system has been established.

Therefore, hithereto, various studies have also been made for developing an effective agent for curing such intractable deseases due to the diabetes but it is the fact that there are almost no success cases. As one of the studies, there is a search on inhibition substance to aldose reductase enzymes, since the enzyme reduces in vivo of human and other animals, aldoses such as glucose and galactose into corresponding polyols such as sorbitol and galactitol and it has been known that said complications will appear when the formed sorbitol and galactitol are accumulated at crystalline lens, peripheral nerve, kidney or the like in patients with diabetes or galactosemia ["Jap. J. Opthalmol." Vol. 20, page 399 (1976); "Int. Congr. Ser. Excerpta Med." Vol. 403, page 594 (1977); and "Metabolism" Vol. 28, page 456 (1979)].

SUMMARY OF THE INVENTION

An object of the invention lies in providing a novel inhibition substance to aldose reductase enzymes to prevent an accumulation of sorbitol and galactitol in vivo and in turn to make prevention and curing of complications due to diabetes possible.

According to the invention, the above object and other objects as will be apparent by fully understanding the invention can be attained by a novel spiro-3-heteroazolidine compound represented by the the formula

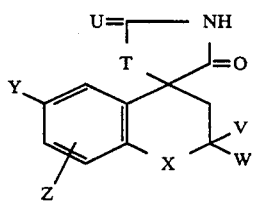 (I)

wherein T represents sulfur atom or hydrogen substituted nitrogen atom, U represents oxygen atom, sulfur atom or imino radical, one of V and W represents hydrogen atom, halogenomethyl radical, 1H-tetrazol-5-yl radical,—COOR,

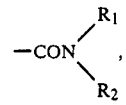

—CH$_2$OR$_3$ or

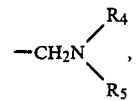

the other of V and W represents hydrogen atom or alkyl group, X represents oxygen atom or sulfur atom, Y and Z are same or different and each represents hydrogen atom, halogen atom, alkyl group, alkoxy group or alkylmercapto group, R is hydrogen atom, alkyl group, —(CH$_2$CH$_2$O)nCH$_3$ or substituted phenyl radical, R$_1$ and R$_2$ are same or different and each represents hydrogen atom, alkyl, —(CH$_2$CH$_2$O)nCH$_3$ or substituted phenyl radical, or R$_1$ and R$_2$ may form together a heterocyclic ring with nitrogen or oxygen atom, R$_3$ is hydrogen atom or alkyl group, R$_4$ and R$_5$ are same or different and each represents hydrogen atom or alkyl group, and n is an integer of 1 to 113, but when T is hydrogen substituted nitrogen atom and U is oxygen atom, there is no case in which one of V and W is hydrogen atom and the other is hydrogen atom or alkyl group and salt thereof.

Namely, it has been confirmed that the compounds (I) have an effective inhibition action to aldose reductase enzymes and that the toxicity thereof is quite low.

In the compounds (I), the alkyl group may be of straight-chain alkyl radicals, branched-chain alkyl radicals or cycloalkyl radicals. As examples for the straight-chain alkyl radicals, one having 1 to 6 carbon atoms, for instance methyl, ethyl, n-propyl, n-butyl, n-pentyl, n-hexyl and the like may be listed. As the branched-chain alkyl radicals, isopropyl, isobutyl, s-butyl, t-butyl and the like may be listed. As the cycloalkyl radicals, one having three or more carbon atoms, for instance cyclopropyl, cyclobutyl, cyclopentyl, cyclohexyl and the like may be listed. As the halogenomethyl radical, fluoromethyl, chloromethyl, bromomethyl, iodomethyl or the like may be listed. A polyethylene glycol methylate part in the polyethylene gloycol derivatives may have a various mean polymerization degree n but those of n=4, 7, 12, 16, 42 and 113 are may be listed as exemplar one. As substituents for the substituted phenyl radical, chlorine atom, bromine atom, methyl radical, methoxy radical and hydroxy radicals in o, m or p-position may be listed. As examples in

wherein the substituents R$_1$ and R$_2$ represent together the heterocyclic ring with nitrogen or oxygen atom, pyrrolidino, morpholino, piperidino, piperidino and the like radicals may be listed. As examples for alkoxy and alkylmercapto radicals, those having a straight-chain alky radical, for instance methoxy, ethoxy, n-propoxy, n-butoxy, n-pentyloxy, n-hexyloxy or the like as well as methylmercapto, ethylmercapto, n-propylmercapto, n-butylmercapto, n-pentylmercapto, n-hexylmercapto or the like may be listed, and those having a branched-chain alkyl, for instance isopropoxy, isobutoxy, s-butoxy, t-butoxy or the like as well as isopropylmercapto, isobutylmercapto, s-butylmercapto, t-butylmercapto or the like may be listed. As the halogen atom, fluorine, chlorine, bromine and iodine may listed but the fluorine is most preferable.

In the specification, the salt of the compounds (I) means those acceptable for employing the same as an effective component in pharmaceutical agents and as concrete examples, those with cations such as sodium, potassium, calcium, magnesium and the like may be listed.

Each of the compounds (I) according to the invention has two asymmetric carbon atoms in its structure and thus have two kinds of stereo isomers and optical isomers thereof. It should be noted that those are, of course, included in scope of the invention.

According to a process according to the invention, a compound among those shown by the formula (I), wherein the substituents T=NH and U=O, namely the compound represented by the formula

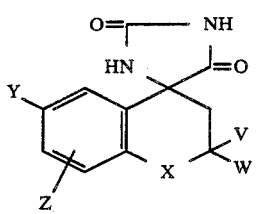

(I-A)

wherein V, W, X, Y and Z have the meanings as referred to can be prepared by reacting a compound represented by the formula

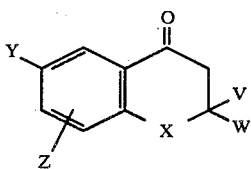

(II)

wherein V, W, X, Y and Z have the meanings as referred to with a metallic cyanide and ammonium carbonate. In this case, sodium cyanide, potassium cyanide and the like may be listed as the metallic cyanide. The reaction may be carried out in the presence of a solvent and at 50° to 150° C. for about 4 hours to 2 days. It may be listed as preferable solvents water, lower alkanols (methanol, ethanol, propanol or the like), lower alkanoamides (acetylamide or the like), cycloethers (dioxane, tetrahydrofuran or the like), lower alkylene glycols (ethylene glycol, triethylene glycol or the like), and N,N-dialkylamides (N,N-dimethylformamide, N,N-diethylformamide or the like). It is sutable to mix the compound (II), metallic cyanide and ammonium carbonate in mol ratio of 1.0:1.2:2.5 to 1:3:8. After completion of the reaction, an aqueous reaction solution (when the solvent is water and if the solvent is not water, the reaction solution diluted with water) is acidified to cause a preciptitation of the objective compound, which means an isolation thereof can easily be carried out.

It may be estimated on preparation of the objective compound (I-A) that two kind isomers will be formed based on the presence of two asymmetric carbon atoms but according to the process of the invention, one of the isomers is predominantly and stereoselectively formed, which can easily be isolated by a mere recystallization and shows excellent pharmaceutical activities of an inhibition on galactitol accumulation and others.

When any of the comopounds (II) as the starting material for the process according to the invention is not available from a market, it can be synthesized by an optional method. For instance, a compound among those shown by the formula (II), wherein the substituents V=H and W=COOH, namely the compound represented by the formula

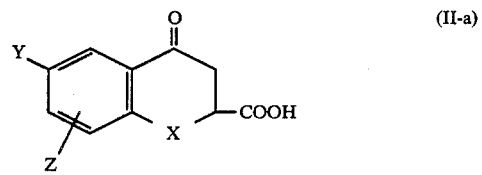

(II-a)

wherein X, Y and Z have the meanings as referred to can be prepared by starting from chromanones ["Ann. Chim."(Rome), 57(10), pages 1045 to 1072 and 58(10), pages 1155 to 1162 (1968)] and in accordance with a following route.

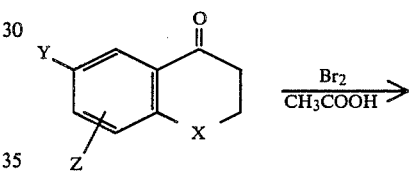

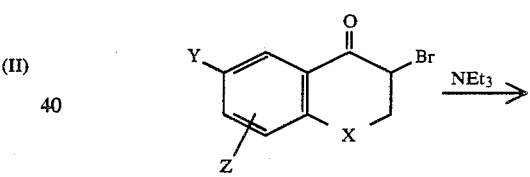

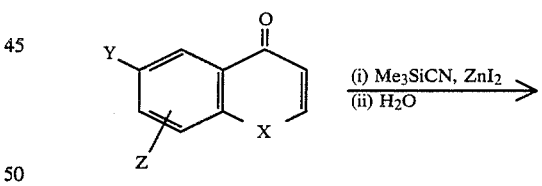

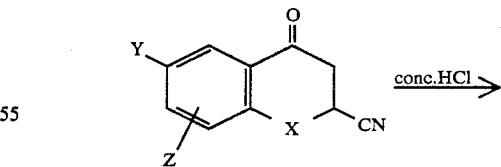

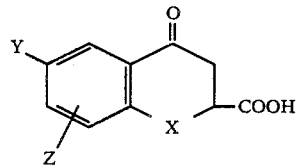

wherein X, Y and Z have the meanings as referred to.

On the other hand, a compound among those shown by the formula (II), wherein the substituents V=CH$_3$ and W=COOH (II-b) can be prepared in accordance with a process as disclosed in "Synthesis" page 886 (1978) and an ester or amide derivative can be synthesized by reacting the compound II-a or II-b with an alcohol or amine.

In synthesizing the ester or carboxamide derivative among the compounds I-A, there is a case that a yield becomes lower, when the corresponding compound of the formula II is directly by hydantoinized. In this case, therefore, it is convenient that in the first place, the compound shown by the formula II-a or II-b is hydantoinized to synthesize corresponding 2-carboxylic acid and then treating the acid to lead into the objective compound. Namely, sulfuric acid, hydrochloric acid or the like mineral acid is acted to the carboxylic acid in methanol, ethanol, propanol or the like alkanol, the carboxylic acid and an alcohol compound are condensed in benzene, toluene or the like non-polar solvent and with use of an aromatic sulfonic acid, or the carboxylic acid and an alcohol compound are condensed with dicyclohexylcarbodiimide or the like condensation agent to form the ester derivative, or the carboxylic acid and an amine are condensed in pyridine, dioxane or the like inert solvent and with use of tetrachlorosilane, dicyclohexylcarbodiimide or the like condensation agent to form the carboxamide derivative.

The hydroxymethyl derivatives, halogenomethyl derivatives, alkoxymethyl derivatives and aminomethyl derivatives can also be prepared by strating from said carboxylic acid. The following is routes for synthesizing the derivatives.

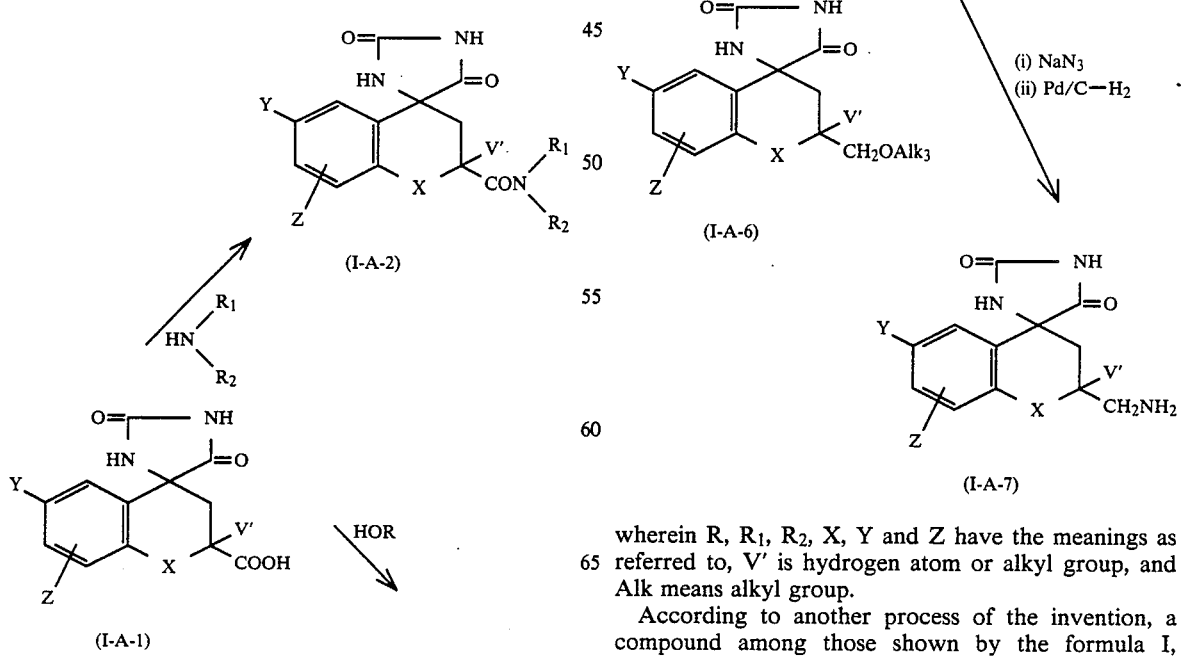

wherein R, $R_1$, $R_2$, X, Y and Z have the meanings as referred to, V' is hydrogen atom or alkyl group, and Alk means alkyl group.

According to another process of the invention, a compound among those shown by the formula I, wherein the substituent T=sulfur atom, namely the compound represented by the formula

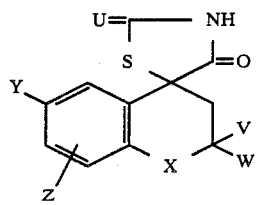
(I-B)

wherein U, V, W, X, Y and Z have the meanings as referred to can be synthesized by starting from the compound represented by the formula

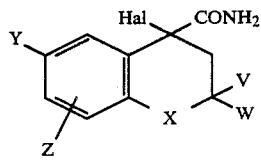
(III)

wherein V, W, X, Y and Z have the meanings as referred to and Hal means a halogen atom.

For instance, the compound among those shown by the formula I-B, wherein the substituent U is imino radical, namely the compound represented by the formula

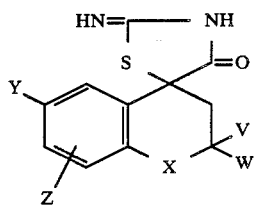
(I-B-1)

wherein V, W, X, Y and Z have the meanings as referred to can be prepared by reacting in the presence of a base the compound of formula III with thiourea. In this case, sodium acetate or the like may be used as the base and acetic acid, cyclic ether (tetrahydrofuran, dioxane or the like), N,N-dialkylamide or the like may be used as a solvent. A reaction temperature for the process is between about 60° and about 150° C. but is preferable to carry out the reaction with use of the acetic acid as the solvent and at its reflux temperature.

The compound among those shown by the formula I-B, wherein the substituent U is oxygen atom, namely the compound represented by the formula

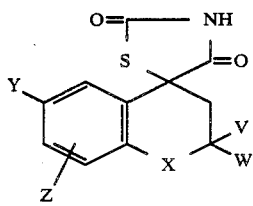
(I-B-2)

wherein V, W, X, Y and Z have the meanings as referred to can be prepared by hydrolizing the compound I-B-1. It is convenient that the hydrolysis is carried out under acidic condition, namely in the presence of a mineral acid and in an alkanol (methanol, ethanol or the like) and at reflux temperature of the solvent.

A compound among those shown by the formula I, wherein the substituents T=hydrogen substituted nitrogen atom and U=sulfur atom, namely the compound represented by the formula

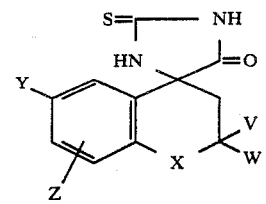
(I-C)

wherein V, W, X, Y and Z have the meanings as referred to can be synthesized by treating the compound III with potassium thiocyanate. This synthetic reaction is carried out at 60° to 150° C. with use of aceton, acetic acid, cyclic ether, N,N-dialkylamide or the like solvent but it is preferable to carry out with use of the acetic acid as solvent and at its reflux temperature.

The compound III as starting material for this process can be prepared with use of a method known per se, for instance by halogenizing with use of thionylchloride, phosphorous tribromide or the like a compound represented by the formula

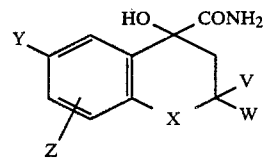
(IV)

wherein V, W, X, Y and Z have the meanings as referred to.

The spiro-3-heteroazolidine compounds according to the invention shows a quite low toxicity of higher than 6000 mg/kg in oral dosage thereof and a high anti- or inhibition activity to aldose reductase enzymes. Especially, 6-fluoro-2,3-dihydro-2',5'-dioxo-spiro(4H-1-benzopyran-4,4'-imidazolidine)-2-carboxamide and 6-fluoro-2,3-dihydro-N,N-dimethyl-2',5'-dioxo-spiro(4H-1-benzopyran-4,4'-imidazolidine)-2-carboxamide are excellent in inhibition of polyol accumuration in sciatic nerve. This leads an assumption that these compounds exert a strong action to the nerve system and thus it may be estimated that the compounds are effective on curing of a peripheral neuropathy which has been considered as an incurable desease among complications due to diabetes. The low toxicity of the compounds according to the invention allows a continuous dosage thereof and this constitutes an important factor for curing chronic complications due to the diabetes.

PREFERRED EMBODIMENTS OF THE INVENTION

The invention will now be further explained with reference to Examples for manufacturing compounds and pharmaceutical preparations according to the invention, as well as Examples showing pharmaceutical properties and effects of the compounds.

REFERENCE EXAMPLE 1

(a) 3-Bromo-6-fluorochromanone

To a solution of 6-fluorochromanone 99.6 g, 0.6 mol) in 500 ml of acetic acid, 96.0 g (0.6 mol) of bromine were added in dropwise at a rate so as to maintain a reaction temperature at 25° C. After stirring the reactants for 2.0 hours at 25° C., the reaction mixture was poured into 1.2 liter of cracked ice with stirring. Resulting precipitate was subsequently filtered, washed with water and then dried on air to give 140 g (95.2%) of the desired compound.

Melting point: 56°–57° C.
IR spectrum ($\nu_{max}^{KBr}$) cm$^{-1}$: 1690, 1620.
NMR spectrum (CDCl$_3$) δ ppm: 4.58 (3H, s), 6.85–7.68 (3H, m).
Mass spectrum (EI/DI) m/z: 244 (M+), 165, 148.

(b) 6-Fluoro-4H-1-benzopyran-4-one

A solution of 3-bromo-6-fluorochromanone (140 g, 0.57 mol)(obtained through the process as described in said Item (a) in 1.5 liter of triethyl-amine was heated at reflux temperature for 1.5 hours. After cooling the reaction mixture, resulting precipitate was filtered and the filtrate was evaporated in vacuo to combine the residue with solids obtained through said filtration. The combined solids were partitioned between 1.2 liter of dichloromethane and 1.2 liter of 2N-hydrochloric acid. An organic layer was washed with water, dried over anhydrous sodium sulfate, filtered and evaporated in vacuo to dryness. Resulting residue was recrystallized from ethyl acetate to give 72.2 g (77.2%) of the desired compound.

Melting point: 165°–168° C.
IR spectrum ($\nu_{max}^{KBr}$) cm$^{-1}$: 1660, 1640, 1620.
NMR spectrum (CDCl$_3$) δ ppm: 6.33 (1H, d, J=6 Hz), 7.17–7.97 (3H, m), 7.82 (1H, d, J=6 Hz).
Mass spectrum (EI/DI) m/z: 164 (M+), 136.

(c) 6-Fluoro-3,4-dihydro-4-oxo-2H-1-benzopyran-2-carbonitrile

To a mixture of 72.2 g (0.44 mol) of 6-fluoro-4H-1-benzopyran-4-one obtained through the process as described in said Item b and 1.39 g (4.4 mmol) of zinc iodide in 610 ml of dry ether, 101 g (1.0 mol) of trimethylsilylcyanide were added under stirring. The mixture was heated at reflux temperature for 24 hours. After cooling the reaction mixture, the solution was poured into 500 ml of methanol, stirred for one hour at room temperature and evaporated in vacuo to dryness. Resulting residue was chromatographed on silica gel, eluting with dichloromethane to give 79.7 g (94.9%) of the desired compound.

Melting point: 87°–89° C.
IR spectrum ($\nu_{max}^{KBr}$) cm$^{-1}$: 1690, 1617.
NMR spectrum (CDCl$_3$) δ ppm: 3.12 (2H, d, J=6 Hz), 5.43 (1H, t, J=6 Hz), 6.83 –7.73 (3H, m).
Mass spectrum (EI/DI) m/z: 191 (M+), 164, 138, 110.

(d) 6-Fluoro-3,4-dihydro-4-oxo-2H-1-benzopyran-2-carboxylic acid

A solution of 6-fluoro-3,4-dihydro-4-oxo-2H-1-benzopyran-2-carbonitrile (78.3 g, 0.41 mol)(obtained through the process as described in said Item (c) in 760 ml of concentrated hydrochloric acid was heated at reflux temperature for 50 minutes. After cooling the reaction solution, 700 ml of water and 1 liter of ethyl acetate were added to carry out an extraction. Resulting organic layer was evaporated in vacuo to dryness. To the residue, 700 ml of saturated sodium biscarbonate was added and stirred for 30 minutes. The aqueous basic solution was washed with 500 ml of ethyl acetate, acidified with 6N-hydrochloric acid and extracted with 1 liter of ethyl acetate. The organic layer was washed with water, dried over anhydrous sodium sulfate, filtered and evaporated in vacuo to give 76.9 g (89.3%) of the desired compound.

Melting point: 163°–164° C.
IR spectrum ($\nu_{max}^{KBr}$) cm$^{-1}$: 1750, 1660.
NMR spectrum (CDCl$_3$) δ ppm: 3.07 (2H, d, J=6 Hz), 5.10 (1H, t, J=6 Hz), 7.11–7.60 (3H, m), 11.33 (1H, broad s).
Mass spectrum (EI/DI) m/z: 210 (M+), 165, 138.

EXAMPLE 1

6-Fluoro-2,3-dihydro-2',5'-dioxo-spiro[4H-1-benzopyran-4,4'-imidazolidine]-2-carboxylic acid A mixture consisting of potassium cyanide (37.1 g, 0.57 mol), ammonium carbonat (164 g, 1.7 mol) and 6-fluoro-3,4-dihydro-4-oxo-2H-1-benzopyran-2-carboxylic acid (60.0 g, 0.29 mol) (obtained through the process as described in the Item d of said Reference Example 1) was heated at 65°–70° C. for 24 hours under stirring and then at reflux temperature for 15 minutes. The reaction mixture was cooled to room temperature and then acidified to pH 1 with concenrated hydrochloric acid. Resulting precipitate was subsequently filtered, washed with water and then recrystallized from water to give 48.8 g (60.1%) of the desired compound.

Melting point: 294°–298° C. (dec.).
IR spectrum ($\nu_{max}^{KBr}$) cm$^{-1}$: 1770, 1750, 1720.
NMR spectrum (DMSO-d) δ ppm: 1.88–2.80 (2H, m), 5.23 (1H, dd), 6.83–7.38 (3H, m), 8.37 (1H, broad s), 11.07 (1H, broad s).
Mass spectrum (EI/DI) m/z: 280 (M+), 262, 234, 219.
Elementary analysis: $C_{12}H_9FN_2O_5$: Cal.: C, 51.43; H, 3.24; N, 10.00. Found: C, 51.15; H, 3.28; N, 9.98.

The compound obtained through said process in this Example was a single diastereoisomer.

From the mother liquor of recrystallization, another diastereoisomer was obtained.

In evaluation of these isomers for ability to reduce or inhibit polyol increase in sciatic nerve of galactosemic rats, the potency of the major diastereoisomer was greater than that of the minor diastereoisomer.

EXAMPLE 2

6-Fluoro-2,3-dihydro-2',5'-dioxo-spiro[4H-1-benzopyran-4,4'-imidazolidine]-2-carboxamide To a solution of 6-fluoro-2,3-dihydro-2',5'-dioxo-spiro[4H-1-benzopyran-4,4'-imidazolidine]-2-carboxylic acid (2.8 g, 0.01 mol) (obtained through the process as described in Example 1) in 30 ml of anhydrous pyridine, 1.2 g (0.006 mol) of silicon tetrachloride were added at temperature below 10° C. After stirring for 15 minutes at room temperature, an excess amount of dry ammonia gas was perfused at temperature below 10° C. The mixture was stirred for 18 hours at room temperature and poured into 100 ml of ethanol. Undissolved matter was filtered off and the filtrate was evaporated to dryness.

To the remaining residue, 20 ml of water was added to stir for 30 minutes at room temperature. A forming precipitate was filtered and subsequently recrystallized from ethanol to give 2.0 g (70.6%) of the desired compound.

Melting point: 286°–300° C. (dec.).

IR spectrum ($\nu_{max}^{KBr}$) cm$^{-1}$: 1770, 1720, 1670.

NMR spectrum (DMSO-d) δ ppm: 1.83–2.67 (2H, m), 5.17 (1H, dd), 6.93–7.33 (3H, m), 7.57, 7.80 (2H, broad s), 8.47 (1H, broad s), 11.07 (1H, broad s).

Mass spectrum (EI/DI) m/z: 279 (M+), 262, 235, 219.

Elementary analysis: $C_{12}H_{10}FN_3O_4$: Cal.: C, 51.62; H, 3.61; N, 15.05. Found: C, 51.79; H, 3.58; N, 14.98.

EXAMPLE 3

6-Fluoro-2,3-dihydro-N-methyl-2',5'-dioxo-spiro[4H-1-benzopyran-4,4'-imidazolidine]-2-carboxamide To a solution of monomethylamine hydrochloride (1.6 g, 0.024 mol) and 6-fluoro-2,3-dihydro-2',5'-dioxo-spiro[4H-1-benzopyran-4,4'-imidazolidine]-2-carboxylic acid (5.6 g, 0.020 mol) (obtained through the process as described in said Example 1) in 60 ml of anhydrous pyridine, 2.4 g (0.024 mol) triethylamine were added at temperature below 0° C., followed by addition of 2.3 g (0.013 mol) of silicon tetrachloride at the same temperature. After stirring the mixture for 18 hours at room temperature, the reaction solution was poured into ethanol. Undissolved matter therein was filtered off and the filtrate was evaporated to dryness. The remaining residue was chromatographed on silica gel, eluting with ethanol to give colorless crystals which were recrystallized from methanol to give 4.2 g (71.2%) of refined desired compound.

Melting point: 297°–300° C. (dec.).

IR spectrum ($\nu_{max}^{KBr}$) cm$^{-1}$: 1775, 1720, 1650.

NMR spectrum (DMSO-d$_6$) δ ppm: 2.00–2.60 (2H, m), 2.68 (3H, d, J=5.0 Hz), 5.07 (1H, dd), 6.67–7.37 (3H, m), 8.00–8.50 (1H, broad s), 8.33 (1H, broad s), 10.07 (1H, broad s).

Mass spectrum (EI/DI) m/z: 293 (M+), 235, 192, 164.

Elementary amalysis: $C_{13}H_{12}FN_3O_4$: Cal.: C, 53.24; H, 4.12; N, 14.33. Found: C, 53.14; H, 3.97; N, 14.16.

EXAMPLE 4

6-Fluoro-N-ethyl-2,3-dihydro-2',5'-dioxo-spiro[4H-1-benzopyran-4,4'-imidazolidine]-2-carboxamide The procedure described in Example 3 was reported except that ethylamine hydrochloride was employed as the starting material in same molar amount (2.72 g, 0.024 mol) in place of monomethylamine hydrochloride. In this particular case, 4.80 g (78.1%) of the desired compound were obtained.

Melting point: above 300° C.

IR spectrum ($\nu_{max}^{KBr}$) cm$^{-1}$: 1780, 1720, 1640.

NMR spectrum (trifluoroacetic acid-d$_1$) δ ppm: 1.36 (3H, t, J=7.0 Hz), 2.33–3.20 (2H, m), 3.62 (2H, q, J=7.0 Hz), 5.62 (1H, dd), 7.00–7.30 (3H, m).

Mass spectrum (EI/DI) m/z: 307 (M+), 235, 192.

Elementary analysis: $C_{14}H_{14}FN_3O_4$: Cal.: C, 54.72; H, 4.59; N, 13.67. Found: C, 54.54; H, 4.55; N, 13.69.

EXAMPLE 5

6-Fluoro-2,3-dihydro-N,N-dimethyl-2',5'-dioxo-spiro[4H-1-benzopyran-4,4'-imidazolidine]-2-carboxamide The procedure described in Example 3 was repeated except that dimethylamine hydrochloride was employed as the starting material in same molar amount (1.96 g, 0.024 mol) in place of monomethlamine hydrochloride. In this particular case, 4.60 g (75.4%) of the desired compound were obtained.

Melting point: 285°–293° C. (dec.).

IR spectrum ($\nu_{max}^{KBr}$) cm$^{-1}$: 1780, 1730, 1640.

NMR spectrum (DMSO-d$_6$) δ ppm: 2.07–2.67 (2H, m), 2.90 (3H, s), 3.07 (3H, s), 5.57 (1H, dd), 6.77–7.20 (3H, m), 8.33 (1H, broad s), 10.03 (1H, broad s).

Mass spectrum (EI/DI) m/z: 307 (M+), 262, 246, 235.

Elementary analysis: $C_{14}H_{14}FN_3O_4$: Cal.: C, 54.72; H, 4.59; N, 13.68. Found: C, 54.73; H, 4.53; N, 13.53.

EXAMPLE 6

6-Fluoro-2,3-dihydro-N-propyl-2',5'-dioxo-spiro[4H-1-benzopyran-4,4'-imidazolidine]-2-carboxamide To a solution of n-propylamine (1.4 g, 0.024 mol) and 6-fluoro-2,3-dihydro-2',5'-dioxo-spiro[4H-1-benzopyran-4,4'-imidazolidine]-2-carboxylic acid (5.6 g, 0.02 mol) (obtained through the process as described in Example 1) in 56.0 ml of anhydrous pyridine, 2.3 g (0.013 mol) of silicon tetrachloride were added at temperature below 20° C. After stirring for 15 hours at room temperature, the reaction mixture was poured into ethanol. Undissolved matter was filtered off and the filtrate was evaporated in vacuo to dryness. The remaining residue was chromatographed on silica gel, eluting with ethanol to give colorless crystals which were recrystallized from methanol to give 5.0 g (77.5%) of the desired refined compound.

Melting point: 282°–284° C.

IR spectrum ($\nu_{max}^{KBr}$) cm$^{-1}$: 1780, 1730, 1680.

NMR spectrum (trifluoroacetic acid-d$_1$) δ ppm: 1.07 (3H, t, J=7.0 Hz), 1.30–2.00 (2H, m), 2.33–3.33 (2H, m), 3.53 (2H, broad t, J=7.0 Hz), 5.58 (1H, dd), 6.96–7.33 (3H, m), Mass spectrum (EI/DI) m/z: 321 (M+), 235, 192.

Elementary analysis: $C_{15}H_{16}FN_3O_4$: Cal.: C, 56.07; H, 5.02; N, 13.08. Found: C, 55.77; H, 5.06; N, 13.12.

EXAMPLE 7

6-Fluoro-2,3-dihydro-N-butyl-2',5'-dioxo-spiro[4H-1-benzopyran-4,4'-imidazolidine]-2-carboxamide The procedure described in Example 6 was repeated except that n-butylamine was employed as the starting material in same molar amount (1.8 g, 0.024 mol) in place of n-propylamine. In this particular case, 4.40 g (65.7%) of the desired compound were obtained.

Melting point: 286°–288° C.

IR spectrum ($\nu_{max}^{KBr}$) cm$^{-1}$: 1775, 1720, 1630.

NMR spectrum (trifluoroacetic acid-d$_1$) δ ppm: 1.03 (3H, broad t, J=7.0 Hz), 1.23–2.10 (4H, m), 2.33–3.33 (2H, m), 3.56 (2H, broad t, J=7.0 Hz), 5.60 (1H, dd), 6.76–7.30 (3H, m).

Mass spectrum (EI/DI) m/z: 335 (M+), 235, 192.

Elementary analysis: $C_{16}H_{18}FN_3O_4$: Cal.: C, 57.31; H, 5.41; N, 12.54. Found: C, 57.10; H, 5.47; N, 12.57.

EXAMPLE 8

6-Fluoro-2,3-dihydro-N-(4-methoxyphenyl)-2',5'-dioxo-spiro[4H-1-benzopyran-4,4'-imidazolidine]-2-carboxamide (a) The procedure described in Example 6 was repeated except that 4-methoxyphenylamine was employed as the starting material in same molar amount (3.0 g, 0.024 mol) in place of n-propylamine. In this particular case, 5.30 g (68.4%) of the desired compound were obtained.

(b) To a solution of 6-fluoro-2,3-dihydro-2',5'-dioxo-spiro[4H-1-benzopyran-4,4'-imidazolidine]-2-carboxylic acid (140 mg, 0.5 mmol) (obtained through the process as described in said Example 1) and 4-methoxyphenylamine (63 mg, 0.5 mmol) in 1.0 ml of N,N-dimethylformamide, a solution of dicyclohexylcarbodiimide (103 mg, 0.5 mmol) in 1.0 ml of N,N-dimethylformamide was added at 5° C. After stirring for 15 hours at room temperature, undissolved matter was filtered off. To the filtrate, 5 ml of 2N-hydrochloric acid were added and the mixture was stirred for 30 minutes. The formed precipitate was filtered and subsequently chromatographed on silica gel, eluting with ethyl acetate to give 78.3 mg (40.7%) of the desired refined compound.

(c) A mixture of 6-fluoro-3,4-dihydro-N-(4-methoxyphenyl)-4-oxo-2H-1-benzopyran-2-carboxamide (220 mg, 0.7 mmol), potassium cyanide (97.5 mg, 1.5 mmol) and ammonium carbonate (400 mg, 4.2 mmol) in 2.1 ml of 60% aqueous ethanol was heated at 65° to 70° C. in a sealed tube for 40 hours. The reaction mixture was diluted with 5.0 ml of water and then acidified with 6N-hydrochloride acid to pH 1. The formed precipitate was filtered and recrystallized from ethanol to give 67.3 mg (25.0%) of the desired compound.

Melting point: 301°–304° C. (dec.).

IR spectrum $(\nu_{max}^{KBr})$ cm$^{-1}$: 3300, 1775, 1730, 1640.

NMR spectrum (DMSO-d$_6$) $\delta$ ppm: 2.00–2.73 (2H, m), 3.73 (3H, s), 5.33 (1H, dd), 6.80–7.80 (7H, m), 8.40 (1H, s), 10.13 (1H, s), 11.07 (1H, broad s).

Mass spectrum (EI/DI) m/z: 385 (M+), 236.

Elementary analysis: $C_{19}H_{16}FN_3O_5$: Cal.: C, 59.22; H, 4.19; N, 10.91. Found: C, 59.01; H, 4.12; N, 10.96.

EXAMPLE 9

6-Fluoro-2,3-dihydro-N-(3,6,9,12-tetraoxatridecyl)-2',5'-dioxo-spiro[4H-1-benzopyran-4,4'-imidazolidine]-2-carboxamide The procedure described in Example 6 was repeated except that 3,6,9,12-tetraoxatridecylamine was employed as the starting material in same molar amount (5.0 g, 0.024 mol) in place of n-propylamine. In this particular case, 7.20 g (77.1%) of the desired compound were obtained.

Melting point: 162°–164° C.

IR spectrum $(\nu_{max}^{KBr})$ cm$^{-1}$: 1770, 1720, 1640.

NMR spectrum (DMSO-d$_6$) $\delta$ ppm: 1.90–2.80 (2H, m), 3.33 (3H, s), 3.30–3.80 (16H, m), 5.23 (1H, dd), 6.90–7.30 (3H, m), 8.25 (1H, broad s), 8.45 (1H, broad s), 11.01 (1H, broad s).

Mass spectrum (EI/DI) m/z: 469 (M+), 305.

Elementary analysis: $C_{21}H_{28}FN_3O_8$: Cal.: C, 53.73; H, 6.01; N, 8.95. Found: C, 53.85; H, 6.19; N, 8.98.

EXAMPLE 10

6-Fluoro-2,3-dihydro-2',5'-dioxo-spiro[4H-1-benzopyran-4,4'-imidazolidine]-2-carboxylic acid methyl ester To a solution of 6-fluoro-2,3-dihydro-2',5'-dioxo-spiro[4H-1-benzopyran-4,4'-imidazolidine]-2-carboxylic acid (2.8 g, 0.01 mol) (obtained through the process as described in Example 1) in 140 ml of methanol, 3.0 ml of concentrated sulfuric acid were added. The mixture was heated at reflux temperature for 1.5 hours, cooled to room temperature and poured into 200 ml of cracked ice with stirring. The formed precipitate was filtered and washed with water to give 2.7 g (91.0%) of the desired refined compound.

Melting point: 291° C.

IR spectrum $(\nu_{max}^{KBr})$ cm$^{-1}$: 1790, 1745, 1730.

NMR spectrum (DMSO-d$_6$) $\delta$ ppm: 2.00–2.83 (2H, m), 3.83 (3H, s), 5.40 (1H, dd), 6.90–7.50 (3H, m), 8.50 (1H, s), 11.77 (1H, broad s).

Mass spectrum (EI/DI) m/z: 294 (M+), 264, 234, 219, 192, 164, 137.

Elementary analysis: $C_{13}H_{11}FN_2O_5$: Cal.: C, 53.06; H, 3.77; N, 9.52. Found: C, 53.07; H, 3.62; N, 9.56.

EXAMPLE 11

6-Fluoro-2,3-dihydro-2',5'-dioxo-spiro[4H-1-benzopyran-4,4'-imidazolidine]-2-carboxylic acid 3,6,9,12-tetraoxatridecyl ester A mixture consisting of 6-fluoro-2,3-dihydro-2',5'-dioxo-spiro[4H-1-benzopyran-4,4'-imidazolidine]-2-carboxylic acid (2.8 g, 0.01 mol) (obtained through the process as described in Example 1), 3,6,9,12-tetraoxatridecanol (2.1 g, 0.01 mol) and p-toluenesulfonic acid (1.9 g, 0.01 mol) in 80 ml of toluene was heated at reflux temperature for 7.0 hours under a Dean-Stark trap. The reaction mixture was evaporated in vacuo to give a semi-solid residue which was partitioned between 50 ml of chloroform and 50 ml of water. The organic layer was dried over anhydrous sodium sulfate, filtered and evaporated in vacuo to give a pale yellow oil which was chromatographed on silica gel, eluting with ethyl acetate to give 3.9 g (82.5%) of the desired refined compound as a colorless oil.

IR spectrum $(\nu_{max}^{neat})$ cm$^{-1}$: 3250, 3070, 2880, 1780, 1720.

NMR spectrum (CDCl$_3$) $\delta$ ppm: 2.47–2.83 (2H, m), 3.37 (3H, s), 3.57–4.00 (14H, m), 4.33–4.60 (2H, m), 5.45 (1H, dd), 6.83–7.30 (3H, m).

Mass spectrum (EI/DI) m/z: 470 (M+), 306.

EXAMPLE 12

6-Fluoro-2,3-dihydro-2-hydroxymethyl-spiro[4H-1-benzopyran-4,4'-imidazolidine]-2',5'-dione To a solution of lithium aluminum hydride (2.3 g, 0.06 mol) in 100 ml of tetrahydrofuran, a solution of 6-fluoro-2,3-dihydro-2',5'-dioxo-spiro[4H-1-benzopyran-4,4'-imidazolidine]-2-carboxylic acid methyl ester (11.7 g, 0.04 mol) (obtained through the process as described in said Example 10) in 100 ml of tetrahydrofuran was added at 5° C. After stirring for 20 hours at room temperature (15° to 20° C.), the reaction mixture was poured into 300 ml of cracked ice with stirring. The aqueous solution was acidified to pH 1 under cooling (10° to 15° C.) by addition of concentrated hydrochloric acid and extracted with 400 ml of ethyl acetate. The organic layer was washed with water, dried over anhydrous sodium sulfate, filtered and evaporated in vacuo to give a solid which was recarystallized from methanol to give 8.7 g (82.0%) of the desired refined compound.

Melting point: 224°–225° C.

IR spectrum ($\nu_{max}^{KBr}$) cm$^{-1}$: 3360, 1760, 1720.

Mass spectrum (EI/DI) m/z: 266 (M+), 248, 219, 205, 192, 164, 137.

Elementary analysis: $C_{12}H_{11}FN_2O_4$: Cal.: C, 54.14; H, 4.16; N, 10.52. Found: C, 53.98; H, 4.34; N, 10.35.

EXAMPLE 13

2-Chloromethyl-6-fluoro-2,3-dihydro-spiro[4H-1-benzopyran-4,4'-imidazolidine]-2',5'-dione To a solution of 6-fluoro-2,3-dihydro-2-hydroxymethyl-spiro[4H-1-benzopyran-4,4'-imidazolidine]-2',5'-dione (2.66 g, 0.01 mol) (obtained through the process as described in said Example 12) in 20 ml of N,N-dimethylformamide, 1.19 g (0.01 mol) of thionylchloride were added, stirred the mixture for 2.0 hours at 20° C. and further stirred for 4 hours at 80° to 85° C. After cooling, the reaction mixture was poured into 100 ml of cracked ice and a forming precipitate was filtered. The precipitate was partitioned between 70 ml of ethyl acetate and 50 ml of water. The organic layer was dried over anhydrous sodium sulfate, filtered and evaporated in vacuo to give a yellowish solid which was chromatographed on silica gel, eluting with ethyl acetate—n-hexane (2:1) to give 2.42 g (85.1%) of the desired refined compound.

Melting point: 212°–214° C.

NMR spectrum (DMSO-d$_6$) δ ppm: 2.33 (2H, m), 4.07 (2H, m), 5.07 (1H, m), 6.93–7.47 (3H, m), 8.53 (1H, broad s), 11.07 (1H, broad s).

Mass spectrum (EI/DI) m/z: 284 (M+), 248, 219, 205, 177, 164, 137.

Elementary analysis: $C_{12}H_{10}ClFN_2O_3$: Cal.: C, 50.63; H, 3.54; N, 9.84. Found: C, 50.77; H, 3.40; N, 9.71.

EXAMPLE 14

6-Fluoro-2-fluoromethyl-2,3-dihydro-spiro[4H-1-benzopyran-4,4'-imidazolidine]-2',5'-dione To a solution of diethylaminosulfur trifluoride (4.09 g, 0.025 mol) in 15 ml of anhydrous tetrahydrofuran, a solution of 6-fluoro-2,3-dihydro-2-hydroxymethyl-spiro[4H-1-benzopyran-4,4'-imidazolidine]-2',5'-dione (3.99 g, 0.015 mol) (obtained through the process as described in said Example 12) in 80 ml of anhydrous tetrahydrofuran was added at temperature below −50° C. The mixture was then warmed to room temperature and stirred for 4.5 hours at room temperature. The solvent was evaporated in vacuo and the remaining residue was partitioned between 40 ml of water and 40 ml of ethyl acetate. The organic layer was washed with water, dried over anhydrous sodium sulfate, and evaporated in vacuo to dryness. The remaining residue was chromatographed on silica gel, eluting with ethyl acetate—n-hexane (1:1) to give 1.43 g (35.5%) of the desired refined compound.

Melting point: 183°–185° C.

IR spectrum ($\nu_{max}^{KBr}$) cm$^{-1}$: 1780, 1730, 1495.

NMR spectrum (DMSO-d$_6$) δ ppm: 1.83–2.43 (2H, m), 3.90–5.47 (3H, m), 6.80–7.43 (3H, m), 8.50 (1H, broad s), 11.03 (1H, broad s).

Mass spectrum (EI/DI) m/z: 268 (M+), 248, 219, 205, 197, 192, 177 164, 137.

EXAMPLE 15

2-Bromomethyl-6-fluoro-2,3-dihydro-spiro[4H-1-benzopyran-4,4'-imidazolidine]-2',5'-dione To a solution of 6-fluoro-2,3-dihydro-2-hydroxymethyl-spiro[4H-1-benzopyran-4,4'-imidazolidine]-2',5'-dione (3.6 g, 0.014 mol) (obtained through the process as described in said Example 12) in 28.0 ml of N,N-dimethylformamide, 3.47 g (0.017 mol) of thionylbromide were added at temperature below 10° C. The mixture was stirred for 2.0 hours at 20° C. and further stirred for 1.5 hours at 80° C. After cooling, the reaction mixture was poured into 40 ml of cracked ice and extracted with ethyl acetate. The organic layer was washed with water, dried over anhydrous sodiumsulfate, filtered and evaporated in vacuo to give a solid which was recrystallized from acetone—n-hexane (1:2) to give 3.40 g (77.3%) of the desired refined compound.

Melting point: 209°–211° C.

IR spectrum ($\nu_{max}^{KBr}$) cm$^{-1}$: 1780, 1740, 1495.

NMR spectrum (DMSO-d$_6$) δ ppm: 1.87–2.43 (2H, m), 3.73–4.03 (2H, m), 4.73–5.20 (1H, m), 6.83–7.47 (3H, m), 8.53 (1H, broad s), 11.05 (1H, broad s).

Mass spectrum (EI/DI) m/z: 328 (M+), 248, 219, 206, 178, 164, 137.

REFERENCE EXAMPLE 2

2-amidomethyl-6-fluoro-2,3-dihydro-spiro[4H-1-benzopyran-4,4'-imidazolidine]-2',5'-dione A mixture consisting of 2-chloromethyl-6-fluoro-2,3-dihydro-spiro[4H-1-benzopyran-4,4'-imidazolidine]-2',5'-dione (4.26 g, 0.015 mol) (obtained through the process as described in said Example 13), sodium iodide (600 mg, 0.004 mol) and sodium adido (1.63 g, 0.023 mol) in 20 ml of N,N-dimethylformamide was heated at reflux temperature for 1.5 hours and then the reaction mixture was poured into 50 ml of cracked ice. The resulting precipitate was filtered and dissolved in ethyl acetate to obtain an extract. The extract was washed with water, dried over anhydrous sodium sulfate, filtered and evaporated in vacuo to give a solid which was chromatographed on silica gel, eluting with ethyl acetate to give 3.06 g (70.1%) of the desired refined compound.

NMR spectrum (DMSO-d$_6$) δ ppm: 2.00–2.40 (2H, dd), 3.56–3.93 (2H, m), 4.83–5.26 (1H, m), 6.86–7.50 (3H, m), 8.48 (1H, s), 11.07 (1H, broad s).

Mass spectrum (EI/DI) m/z: 291 (M+), 248, 192.

EXAMPLE 16

2-Aminomethyl-6-fluoro-2,3-dihydro-spiro[4H-1-benzopyran-4,4'-imidazolidine]-2',5'-dione To a solution of 20% Pd-C (0.6 g, 5.6 mmol) in 20 ml of 50% aqueous ethanol, a solution of 2-adidomethyl-6-fluoro-2,3-dihydro-spiro[4H-1-benzopyran-4,4'-imidazolidine]-2',5'-dione (3.0 g, 0.01 mol) (obtained through the process as described in said Reference Example 2) in 160 ml of ethanol was added at room temperature. The mixture was hydrogenated for 16 hours at atmospheric pressure. After filtration, the filtrate was evaporated in vacuo to give a solid which was recrystallized from ethanol to give 2.5 g (84.0%) of the desired refined compound.

Melting point: 231°–233° C.

IR spectrum ($\nu_{max}^{KBr}$) cm$^{-1}$: 1775, 1725.

NMR spectrum (DMSO-d$_6$) δ ppm: 1.90–2.30 (2H, m), 2.82 (2H, d), 4.33–5.00 (1H, m), 4.83–6.00 (1H, broad), 6.77–7.43 (3H, m).

Mass spectrum (EI/DI) m/z: 265 (M+), 248.

Elementary analysis: C$_{12}$H$_{12}$FN$_3$O$_3$: Cal.: C, 54.34; H, 4.56; N, 15.84. Found: C, 54.03; H, 4.52; N, 15.45.

REFERENCE EXAMPLE 3

4-Chloro-6-fluoro-3,4-dihydro-2H-1-benzopyran-4-carboxamide

A mixture consisting of 6-fluoro-4-hydroxy-3,4-dihydro-2H-1-benzopyran-4-carboxamide (60 mg, 0.28 mmol) and thionylchloride (60 mg, 0.28 mmol) in 1.0 ml of diethyl ether was stirred for 5.0 hours at 28° C. The reaction mixture was evaporated in vacuo to give a pale yellowish oil which was chromatographed on silica gel, eluting with ethyl ether to give 43 mg (67.2%) of the desired refined compound.

Melting point: 93°–95° C.

IR spectrum ($\nu_{max}^{KBr}$) cm$^{-1}$: 3480, 3420, 1680.

NMR spectrum (CDCl$_3$) δ ppm: 2.10–2.57 (1H, m), 2.73–3.33 (1H, m), 4.39 (2H, m), 6.50–7.27 (5H, m).

Mass spectrum (EI/DI) m/z: 229 (M+), 193, 185.

EXAMPLE 17

6-Fluoro-2,3-dihydro-2'-thioxo-spiro[4H-1-benzopyran-4,4'-imidazolidine]-5'-one

A mixture consiting of 4-chloro-6-fluoro-3,4-dihydro-2H-1-benzopyran-4-carboxamide (10.0 g, 0.044 mol) (obtained through the process as described in said Reference Example 3) and potassium thiocyanate (13.4 g) in 150 ml of acetic acid was heated at reflux temperature for 2.5 hours. The reaction mixture was evaporated in vacuo to dryness and the remaining residue was partitioned between 100 ml of ethyl acetate and 100 ml of water. The organic layer was dried over anhydrous sodium sulfate, filtered and evaporated in vacuo to dryness. The remaining residue was chromatographed on silica gel, eluting with ethyl ether-n-hexane (1:1) to give 9.3 g (83.7%) of the desired refined compound.

Melting point: 149°–153° C.

IR spectrum ($\nu_{max}^{KBr}$) cm$^{-1}$: 3450, 1745.

NMR spectrum (CDCl$_3$) δ ppm: 2.13–2.52 (2H, m), 4.10–4.83 (2H, m), 6.56–7.17 (3H, m), 8.33 (1H, broad s), 9.60 (1H, broad s).

Mass spectrum (EI/DI) m/z: 252 (M+), 193, 165.

PHARMACEUTICAL AGENT PREPARATION EXAMPLE 1

A dry solid pharmaceutical composition was prepared by blending following materials together.

| Product of Example 2 | 50 parts by weight |
| --- | --- |
| Sidium citrate | 25 |
| Alginic acid | 10 |
| Polyvinylpyrrolidone | 10 |
| Magnesium stearate | 5 |

After throughly blended the dry composition, 1000 tablets were punched from the resulting mixture, each of which has a size so as to contain 50 mg of the active ingredient.

PHARMACEUTICAL AGENT PREPARATION EXAMPLE 2

Tablets were prepared by the procedure similar to that as described in said Pharmaceutical Agent Preparation Example 1, except that the product of Example 1 was employed as the active ingredient in the place of the product of Example 2.

Each tablet contained 50 mg of the product of Example 1, as the active ingredient.

PHARMACEUTICAL AGENT PREPARATION EXAMPLE 3

Tablets were prepared by the procedure simlar to that as described in said Pharmaceutical Agent Preparation Example 1, except that the product of Example 3 was employed as the active ingredient in the place of the product of Example 2.

Each tablet contained 50 mg of the product of Example 3, as the active ingredient.

PHARMACEUTICAL AGENT PREPARATION EXAMPLE 4

Tablets were prepared by the procedure similar to that as described in said Pharmaceutical Agent Preparation Example 1, except that the product of Example 5 was employed as the active ingredient in the place of the product of Example 2.

Each tablet contained 50 mg of the product of Example 5, as the active ingredient.

PHARMACEUTICAL AGENT PREPARATION EXAMPLE 5

Tablets were prepared by the procedure similar to that as described in said Pharmaceutical Agent Preparation Example 1, except that the product of Example 8 was employed as the active ingredient in the place of the product of Example 2.

Each tablet contained 50 mg of the product of Example 8, as the active ingredient.

PHARMACOLOGICAL TEST EXAMPLE 1

Some spiro-3-heteroazolidine compounds according to the invention were tested to evaluate their ability on reduction or inhibition of aldose reductase enzyme activity, in accordance with the procedure proposed by Kador and Sharpless ["Biophysical Chemistry" 8, 81 (1978)].

Using water-soluble extracts of rat lenses, the inhibitions of these compounds were determined. Results are shown in following Table 1 in terms of percent inhibition of enzyme activity with respect to various concentrations of $10^{-5}$–$10^{-8}$M. IC$_{50}$ represents the concentration of inhibitor which gives 50% inhibition.

TABLE 1

| Compound | Percent Inhibition (%) | | | | IC$_{50}$ (M) |
| --- | --- | --- | --- | --- | --- |
| Product of Example | $10^{-8}$ M | $10^{-7}$ M | $10^{-6}$ M | $10^{-5}$ M | |
| 1 | | 9 | 47 | 77 | $6.0 \times 10^{-6}$ |
| 2 | | 15 | 85 | 93 | $4.0 \times 10^{-7}$ |
| 3 | | 26 | 78 | 71 | $5.0 \times 10^{-7}$ |
| 5 | | 10 | 29 | 61 | $5.0 \times 10^{-6}$ |
| 8 | 14 | 65 | 81 | 81 | $7.0 \times 10^{-8}$ |
| 12 | | 13 | 28 | 85 | $4.0 \times 10^{-6}$ |
| 13 | | 3 | 51 | 90 | $1.0 \times 10^{-6}$ |

PHARMACOLOGICAL TEST EXAMPLE 2

Some spiro-3-heteroazolidine compounds according to the invention were tested to evaluate their ability on reduction or inhibition of polyol increase in sciatic nerve of galactosemic rats. To the rats, 30% galactose diet was fed and said compounds were orally administered at a dose of 10 mg/kg once a day for a period of 8 days. Control animals were received the galactose diet and were administered no such compound. One day after final administration (on 9th day from the first administration), sciatic nerves were removed for galactitol determination.

Results are shown in following Table 2 in terms of percent inhibition as compared to galactitol increase of the control animals.

TABLE 2

| Compound | Percent Inhibition (%) |
| --- | --- |
| Product of Example | |
| 1 | 36 |
| 2 | 85 |
| 3 | 31 |
| 5 | 70 |
| 8 | 26 |
| 12 | 40 |
| 13 | 88 |

We claim:

1. A spiro-3-heteroazolidine compound of the formula

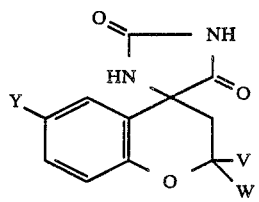

wherein
one of V and W is a hydrogen atom and the other is a halomethyl, hydroxymethyl or aminomethyl radical, a carboxyl or methyl carboxylate radical, or a —(CH$_2$CH$_2$O)$_4$CH$_3$ radical, or a

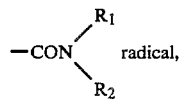

(in which R$_1$ and R$_2$ are the same or different and each is a hydrogen atom, an alkyl group having 1 to 4 carbon atoms, a —(CH$_2$CH$_2$O)$_4$CH$_3$ radical, or a methoxyphenyl radical),
and wherein Y is a halogen atom,
or a pharmaceutically acceptable salt thereof.

2. A compound as claimed in claim 1, wherein said compound is 6-fluoro-2,3-dihydro-2',5'-dioxo-spiro[4H-1-benzopyran-4,4'-imidazolidine]-2-carboxylic acid.

3. A compound as claimed in claim 1, wherein said compound is 6-fluoro-2,3-dihydro-2',5'-dioxo-spiro[4H-1-benzopyran-4,4'-imidazolidine]-2-carboxylic acid methyl ester.

4. A compound as claimed in claim 1, wherein said compound is 6-fluoro-2,3-dihydro-2',5'-dioxo-spiro[4H-1-benzopyran-4,4'-imidazolidine]-2-carboxylic acid 3,6,9,12-tetraoxatridecyl ester.

5. A compound as claimed in claim 1, wherein said compound is 6-fluoro-2,3-dihydro-2',5'-dioxo-spiro[4H-1-benzopyran-4,4'-imidazolidine]-2-carboxamide.

6. A compound as claimed in claim 1, wherein said compound is 6-fluoro-2,3-dihydro-N-methyl-2',5'-dioxo-spiro[4H-1-benzopyran-4,4'-imidazolidine]-2-carboxamide.

7. A compound as claimed in claim 1, wherein said compound is 6-fluoro-2,3-dihydro-N,N-dimethyl-2',5'-dioxo-spiro[4H-1-benzopyran-4,4'-imidazolidine]-2-carboxamide.

8. A compound as claimed in claim 1, wherein said compound is 6-fluoro-N-ethyl-2,3-dihydro-2',5'-dioxo-spiro[4H-1-benzopyran-4,4'-imidazolidine]-2-carboxamide.

9. A compound as claimed in claim 1, wherein said compound is 6-fluoro-2,3-dihydro-N-propyl-2',5'-dioxo-spiro[4H-1-benzopyran-4,4'-imidazolidine]-2-carboxamide.

10. A compound as claimed in claim 1, wherein said compound is 6-fluoro-N-butyl-2,3-dihydro-2',5'-dioxo-spiro[4H-1-benzopyran-4,4'-imidazolidine]-2-carboxamide.

11. A compound as claimed in claim 1, wherein said compound is 6-fluoro-2,3-dihydro-N-(4-methoxyphenyl)-2',5'-dioxo-spiro[4H-1-benzopyran-4,4'-imidazolidine]-2-carboxamide.

12. A compound as claimed in claim 1, wherein said compound is 6-fluoro-2,3-dihydro-N-(3,6,9,12-tetraoxatridecyl)-2',5'-dioxo-spiro[4H-1-benzopyran-4,4'-imidazolidine]-2-carboxamide.

13. A compound as claimed in claim 1, wherein said compound is 6-fluoro-2,3-dihydro-2-hydroxymethyl-spiro[4H-1-benzopyran-4,4'-imidazolidine]-2',5'-dione.

14. A compound as claimed in claim 1, wherein said compound is 2-chloromethyl-6-fluoro-2,3-dihydro-spiro[4H-1-benzopyran-4,4'-imidazolidine]-2',5'-dione.

15. A compound as claimed in claim 1, wherein said compound is 6-fluoro-2-fluoromethyl-2,3-dihydro-spiro[4H-1-benzopyran-4,4'-imidazolidine]-2',5'-dione.

16. A compound as claimed in claim 1, wherein said compound is 2-bromomethyl-6-fluoro-2,3-dihydro-spiro[4H-1-benzopyran-4,4'-imidazolidine]-2',5'-dione.

17. A compound as claimed in claim 1, wherein said compound is 2-aminomethyl-6-fluoro-2,3-dihydro-spiro[4H-1-benzopyran-4,4'-imidazolidine]-2',5'-dione.

18. A pharmaceutical composition for preventing and curing a complication in diabetes, which comprises an effective amount of a spiro-3-heteroazolidine compound of the formula

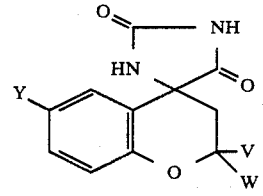

wherein
one of V and W is a hydrogen atom and the other is a halomethyl, hydroxymethyl or aminomethyl radical, a carboxyl or methyl carboxylate radical, or a —(CH$_2$CH$_2$O)$_4$CH$_3$ radical, or a

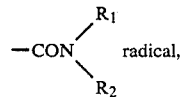

(in which $R_1$ and $R_2$ are the same or different and each is a hydrogen atom, an alkyl group having 1 to 4 carbon atoms, a $-(CH_2CH_2O)_4CH_3$ radical, or a methoxyphenyl radical), and wherein Y is a halogen atom, or a pharmaceutically acceptable salt thereof in combination with a pharmaceutically acceptable carrier.

19. The pharmaceutical composition as claimed in claim 18, wherein said spiro-3-heteroazolidine compound is selected from the group consisting of
6-fluoro-2,3-dihydro-2',5'-dioxo-spiro[4H-1-benzopyran-4,4'-imidazolidine]-2-carboxamide,
2-chloromethyl-6-fluoro-2,3-dihydro-spiro[4H-1-benzopyran-4,4'-imidazolidine]-2',5'-dione, and
2-bromomethyl-6-fluoro-2,3-dihydro-spiro[4H-1-benzopyran-4,4'-imidazolidine]-2',5'-dione.

20. The pharmaceutical composition as claimed in claim 18, wherein said spiro-3-heteroazolidine compound is selected from the group consisting of
6-fluoro-2,3-dihydro-N-methyl-2',5'-dioxo-spiro[4H-1-benzopyran-4,4'-imidazolidine]-2-carboxamide,
6-fluoro-2,3-dihydro-N-(4-methoxyphenyl)-2',5'-dioxospiro[4H-1-benzopyran-4,4'-imidazolidine]-2-carboxamide,
6-fluoro-2,3-dihydro-N-(3,6,9,12-tetraoxatridecyl)-2',5'-dioxo-spiro[4H-1-benzopyran-4,4'-imidazolidine]-2-carboxamide,
6-fluoro-2,3-dihydro-2',5'-dioxo-spiro[4H-1-benzopyran-4,4'-imidazolidine]-2-carboxylic acid methyl ester,
6-fluoro-2,3-dihydro-2',5'-dioxo-spiro[4H-1-benzopyran-4,4'-imidazolidine]-2-carboxylic acid 3,6,9,12-tetraoxatridecyl ester, and
6-fluoro-2-fluoromethyl-2,3-dihydro-spiro[4H-1-benzopyran-4,4'-imidazolidine]-2',5'-dione.

* * * * *